United States Patent [19]

Celmer et al.

[11] 4,062,945

[45] Dec. 13, 1977

[54] POLYCYCLIC ETHER ANTIBIOTIC

[75] Inventors: Walter D. Celmer, New London; Walter P. Cullen, East Lyme; Charles E. Moppett; John R. Oscarson, both of Groton; John R. Routien, Lyme, all of Conn.

[73] Assignee: Pfizer Inc., New York, N.Y.

[21] Appl. No.: 662,701

[22] Filed: Mar. 1, 1976

Related U.S. Application Data

[62] Division of Ser. No. 548,421, Feb. 10, 1975, Pat. No. 4,002,885.

[51] Int. Cl.² ............................................. A61K 35/74
[52] U.S. Cl. ..................................................... 424/122
[58] Field of Search ......................................... 424/122

*Primary Examiner*—Jerome D. Goldberg
*Attorney, Agent, or Firm*—Connolly and Hutz

[57] ABSTRACT

A new polycyclic ether antibiotic with anticoccidial, insecticidal and antimicrobial activity, its production by fermentation and methods for its recovery and purification are described.

5 Claims, 5 Drawing Figures

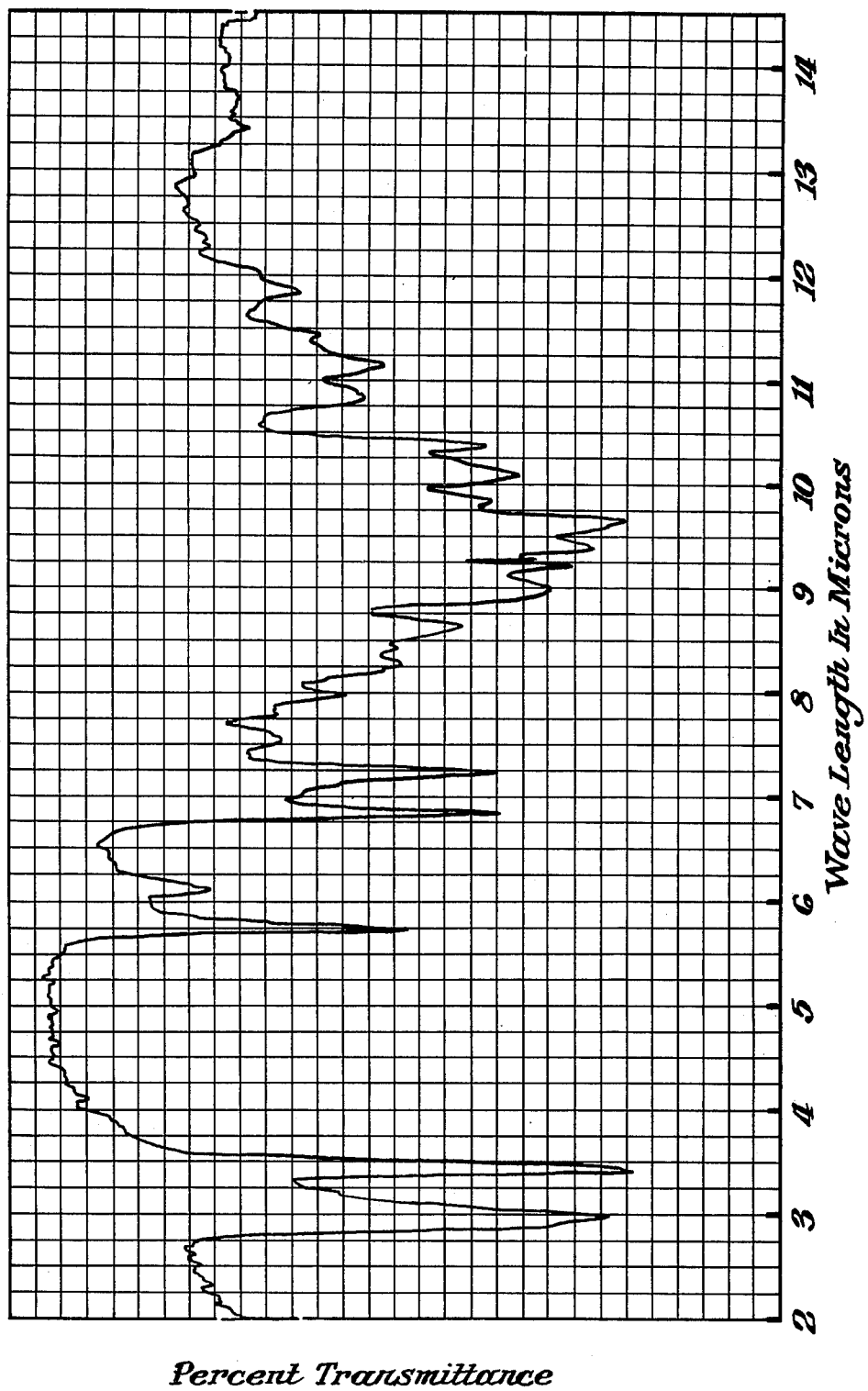

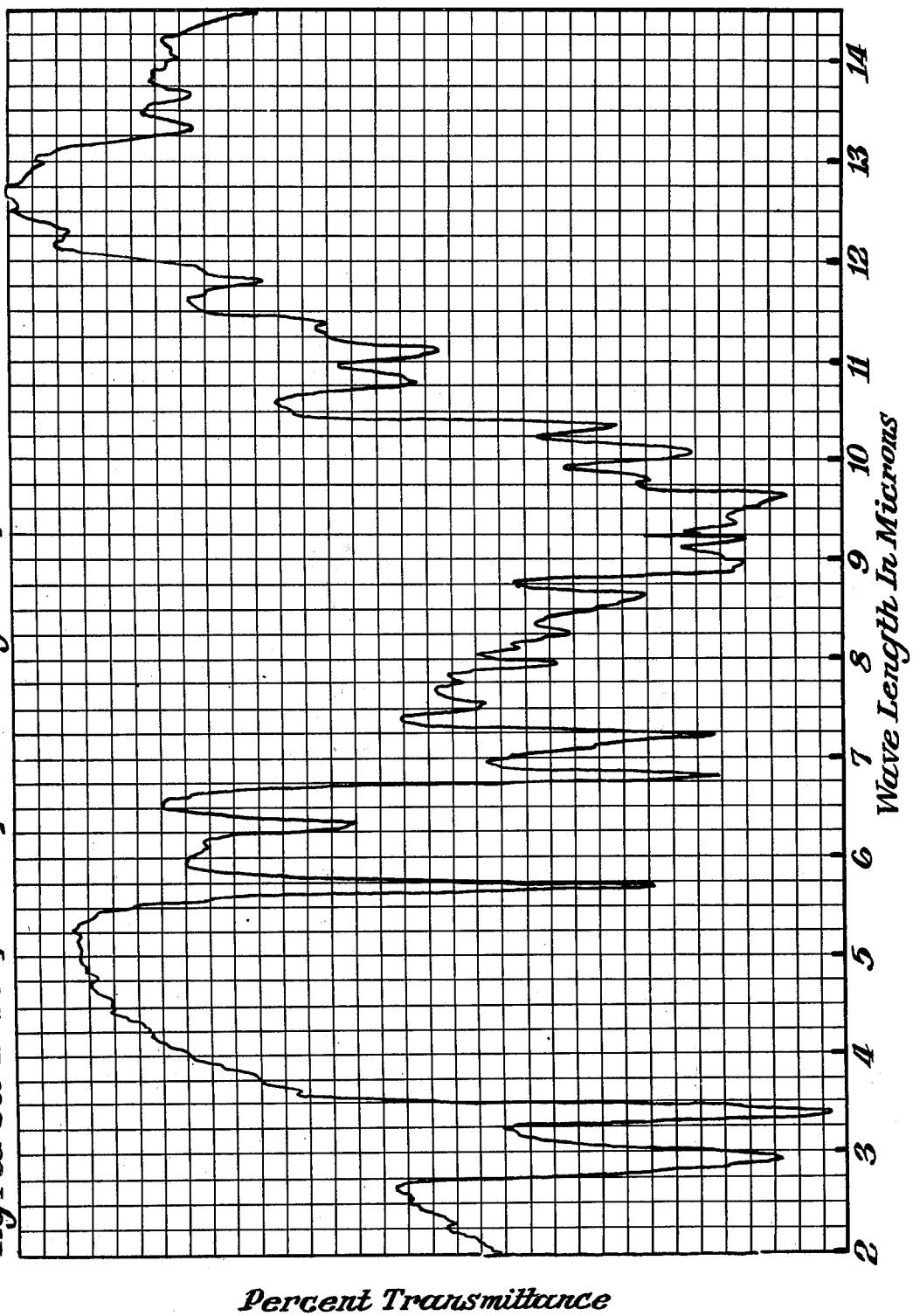

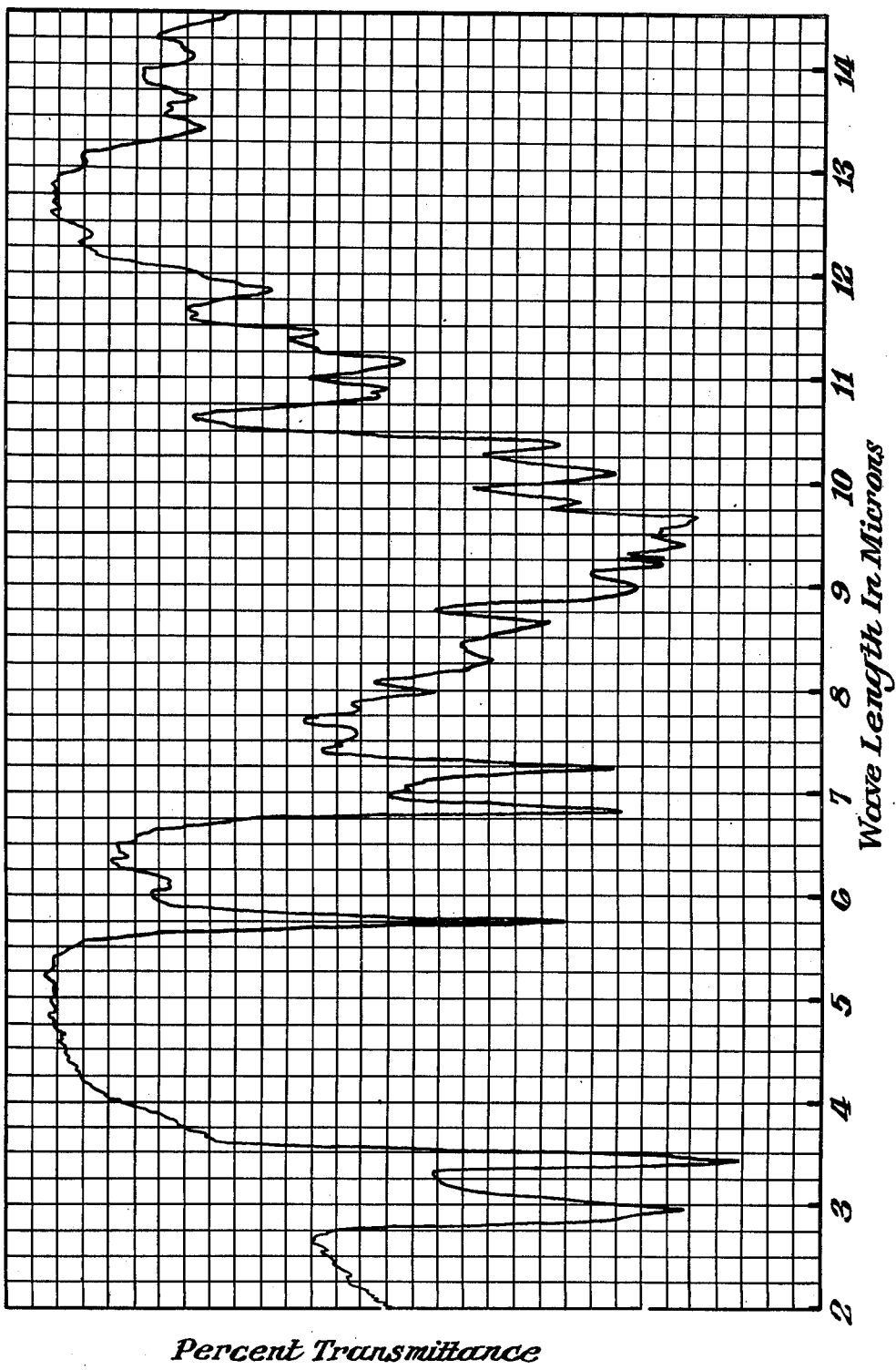

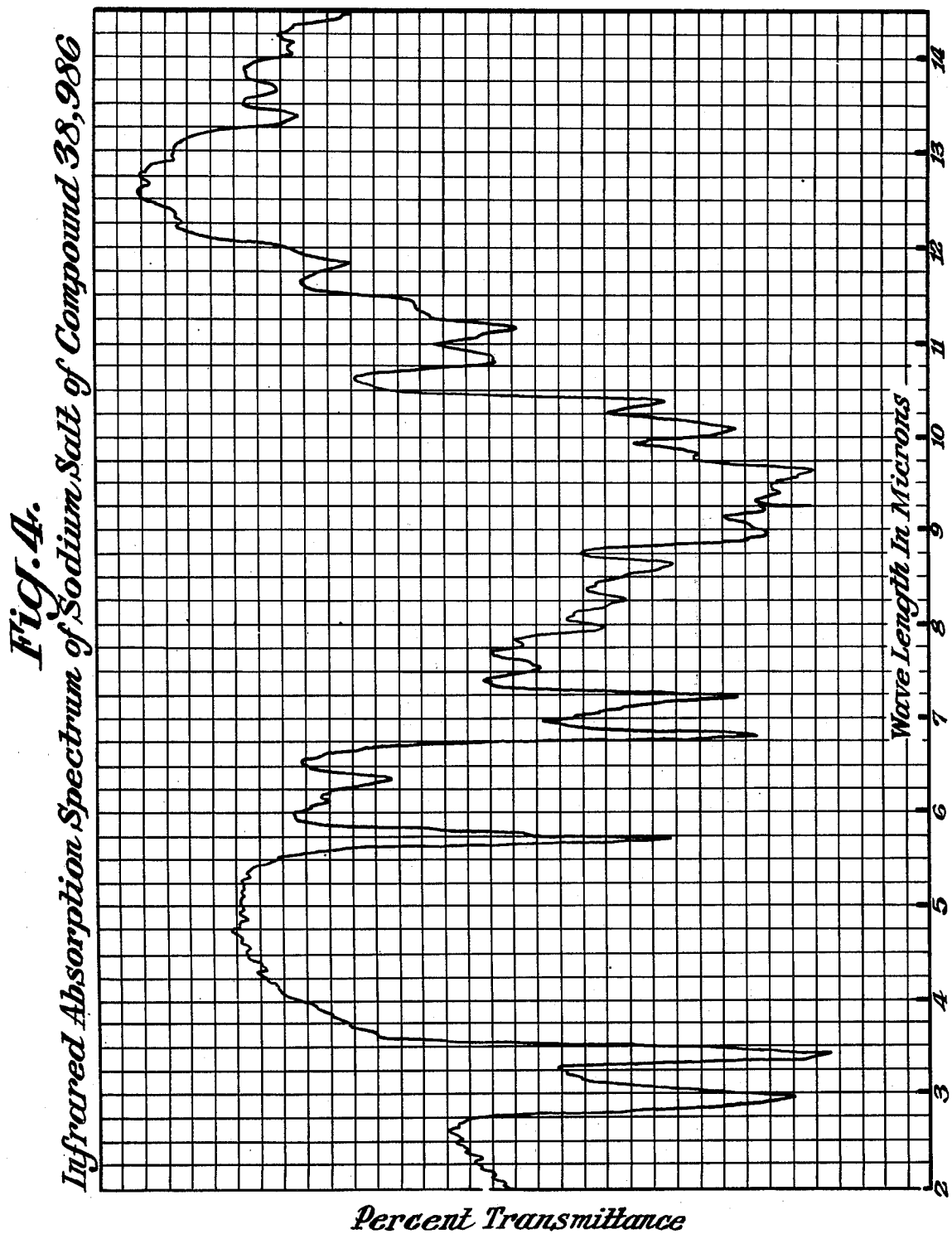

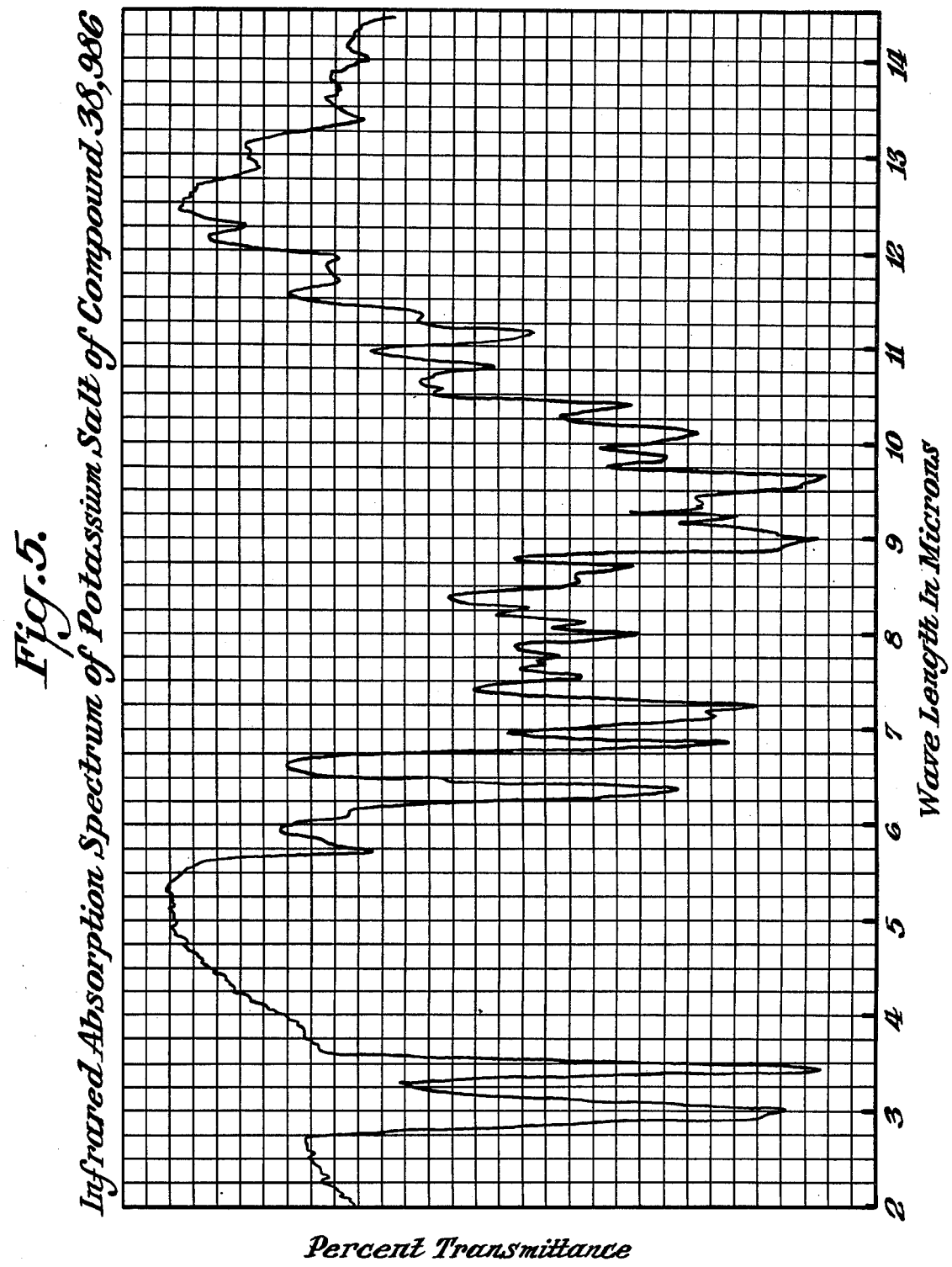

POLYCYCLIC ETHER ANTIBIOTIC

CROSS REFERENCE TO RELATED APPLICATION

This application is a divisional of application Ser. No. 548,421 filed Feb. 10, 1975, now U.S. Pat. No. 4,002,885.

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin (J. Amer. Chem. Soc., 89:5737, 1957); nigericin (Biochem. Biophys, Res. Comm., 33:29, 1968); grisorixin (J. Chem. Soc. Chem. Commun., 1421, 1970); dianerycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399, 1973).

The polycyclic ether antiboiotics listed above are active against Gram-positive bacteria, fungi and protoza. These antibiotics exhibit potent anticoccidial activity.

The control of coccidiosis continues to be a serious problem to the poultry industry. There are six species of coccidia which produce easily discernible morbidity in susceptible chickens. *Eimeria tenella, E. necatrix. E. brunetti, E. acervulina, E. maxima* and *E. mivati* produce damage either directly through destruction of epithelial cells of the digestive tract or indirectly through production of toxins. Three other species of protoza belonging to the same genus are considered to be relatively innocuous; however, *E. mitis, E. hagani* and *E. praecox* are capable of reducing weight gain, lowering feed efficiency and adversely affecting egg production.

The polycyclic ether antibiotics possess a high degree of effectiveness against all species of Eimeria. These antibiotics can, therefore, be regarded as "broad spectrum" coccidiostats.

SUMMARY OF THE INVENTION

This invention is concerned with a new acidic polycyclic ether antibiotic produced by the submerged aerobic propagation in aqueous nutrient media of *Streptomycea flaveolus* ATCC 31100 Isolated from a soil sample from Japan. The antibiotic and its cationic salts are active against a variety of microorganisms and are effective in controlling coccidiosis in poultry. In addition to the above effects, this antibiotic and its metallic salts also possess insecticidal activity.

DETAILED DESCRIPTION OF THE INVENTION

The antibiotic producing microorganism of the present invention was found on examination to have the morphological features of a Streptomyces. It was, therefore, planted on media designated for the International Streptomyces Project descriptive work by Shirling and Gottlieb in International Journal Systematic Bacteriology, 16:313-340, 1966 and also on a number of other media frequently used in identification and compared with *Streptomyces flaveolus* ATCC 3319.

Incubation was at 28° C. except where noted otherwise, and results were recorded at appropriate times; results given here are after two weeks of incubation except where otherwise noted.

The media and reference to their composition are listed as follows:

1. Czapek-Sucrose Agar: Waksman, *The Actinomycetes*, Vol. II, 1961, medium no. 1, p. 328.
2. Glucose-Asparagine Agar: Waksman, The Actinomycetes, Vol. II, 1961, medium no. 2, p. 328.
3. Calcium Malate Agar: Waksman, *Bact. Reviews*, 21:1-29, 1957.
4. Nutrient Agar: Waksman, *The Actinomycetes*, Vol. II, 1961, medium no. 14, p. 330.
5. Yeast Extract- Malt Extract Agar: Pridham et al., *Antibiotics Annual*, 1956/1957: 947-953.
6. Gelatin: Gordon and Mihm, *J. Bact.*, 73:15-27, 1957.
7. Starch Agar:

| | |
|---|---|
| Potato Starch | 20.0 g |
| $NH_4Cl$ | 0.5 g |
| Distilled Water | 1 liter |
| Agar | 15 g |
| pH 7.0 | |

8. Oatmeal Agar: 30 g Quaker Oats steamed in 1000 ml distilled water for 30 minutes, strained, volume restored to 1 liter, pH adjusted to 6.5-7.0 and 15 g agar added.
9. Tryptone Yeast Extract Broth: Pridham and Gottlieb, *J. Bact.*, 56:107-114, 1948.
10. Cellulose: Jensen, *Proc. Linnean Soc. N. S. Wales*, 55:231-248, 1930, and medium no. 2511 in Levine and Schoenlein's *A Compilation of Culture Media for the Cultivation of Microorganisms*, 1930.
11. Dextrose Nitrate Broth: Waksman, *The Actinomycetes*, Vol. II, 1961, medium no. 1 on p. 328 without agar.
12. Organic Nitrate Broth: Gordon and Mihm, *J. Bact.*, 73:15-27, 1957.
13. Skimmed Milk: Difco.
14. Peptone Iron Agar: Difco.
15. Potato Plugs: Plugs placed in tubes containing a glass ring at the bottom and about 0.5 ml water and autoclaved at 121° C. for 20 minutes.
16. Carbon Utilization: Pridham and Gottlieb, *J. Bact.*, 56:107-114, 1948.

The new culture (Pfizer F.D. 24306) was described as follows on the various media (color with all of names capitalized are those of Ridgway, *Color Standards And Nomenclature*, 1912):

| Medium | Growth | Aerial Mycellum | Reverse | Soluble Pigment |
|---|---|---|---|---|
| Gelatin | Good, flat | Cream colored with gray developing in the center. | Light yellow | Lacking |
| Glucose-Asperagine Agar | Poor to moderate, flat, creamy yellow color, soft | Lacking | Creamy yellow color | Lacking |
| Czapek- | Good, slightly | White but becoming | Creamy yellow | Pale yellow |

| Medium | Growth | Aerial Mycellum | Reverse | Soluble Pigment |
|---|---|---|---|---|
| Sucrose Agar | raised; earthy odor | pale gray around edge of colony | | |
| Nutrient Agar | Moderate, flat | White | Yellow | Lacking |
| Yeast extract-malt extract Agar | Good, raised; earthy odor | Fluffy to cottony, near Light Olive Gray | Yellowish brown | Pale brown |
| Oatmeal Agar | Excellent, flat; faint fruity odor | Lacking except at edges of colony where it was slightly raised and near Pale Mouse Gray. | Whitish gray | Lacking |
| Calcium Malate Agar | Moderate, slightly raised; faint fruity odor; malate digested | Slightly cottony surface, near Olive Gray | Whitish gray | Lacking |

Skimmed Milk-No. coagulation in 21 days; complete hydrolysis between 14th and 21st days, pH changed from 6.5–6.7 to 7.1 after 21 days; pinkish tan soluble pigmeat.

Potato Plugs — Growth moderate with slight roughening and white bloom on surface; gray soluble pigment.

Spores — Oatmeal agar plates revealed chales of spores scattered along the bypass as loops, hooks and spirals of one to several moderately tight turns, 10–50, spores per chain. Spores were broadly elliptical to nearly round, $1.1 \times 1.1$ to $2.7 \times 1.6$ but mostly $1.6 \times 1.6$ g. roughened as if with short spires (compound microscope, 1000 ×); with scanning electron microscope projections on the surface of the space were like those shown in FIG. 38 is Int. Jr. System, Esct. 15: 60-159, 1965 of carbon replica of hairy spores of Streptomyces flavcolus. Spores at first were separated by connections narrower than the spores, but continued incubation for several weeks resulted in disappearance of connective cells.

Biochemical Properties — No retaining production; $H_2S$ produced in three days; gelatin liquified, starch hydrolysis only as a clear area under the colony; nitrate reduced to nitrite in dextrose nitrite broth but not in organic nitrate broth; good growth on cellulose strips but no disintegration; utilization of glucose, 1.(−) arabiaose, dextrin, D(−) fructose, D(+) galactose, glycerol, isositol, isulin, lactose, maltose, D(−) michitol, raffinose, thacaose, salicin, D(−) sorbitol, starch, sucrose, trehalose, D(−)xylose; dulcitol not uilized; utilization of sorbose doubtful.

The new culture and the type strain Streptomyces fluaveolus ATCC 3319 were essentially alike on plates of media for morphological study; showed no color change in the soluble pigment when the pH was changed, showed the same type of spore ornamentation, the same carbon utilization pattern and nearly the same biochemical properties.

The greatest difference between the two cultures were reduction of nitrate to nitrite in organic nitrate broth and the production of a bright yellow soluble pigment on many media by Streptomyces flaveolus ATCC 3319; minor differences in color or form of growth of the two cultures were noted.

The new culture (Pfizer F.D. 24306) was submitted to the American Type Culture Collection in Rockville, Md. on Nov. 15, 1974 and given the disignation Streptomyces flaveolus ATCC 31100. The permanency of the deposit and ready accessibility thereto by the public are afforded in the event the patent is granted. Access to the culture is available during pendency of the application under Rule 14 and 35 USC 112. All restrictions on the availability to the public of the culture deposited will be irrevocably removed upon granting of the patent.

Cultivation of Streptomyces flaveolus ATCC 31100 preferably takes place in aqueous nutrient media at a temperature of 28–36° C., and under submerged aerobic conditions with agitation. Nutrient media which are useful for such purposes include a source of assimilable carbon such as augars, starches and glycerol; a source of organic nitrogen such as casein, enzymatic digest of casein, soybean meal, cotton seed meal, peanut meal, wheat gluten, soy flour, meat meal and fish meal. A source of growth substances such as grain soulables and yeast extract as well as salts such as sodium chloride and calcium carbonate and trace elements such as iron, magnesium, zinc, cobalt and manganese may also be utilized with advantageous results. If escessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seed from the shake flasks. Growth in shaken flasks will generally have reached its maximum in 3 to 5 days whereas inoculum in submerged inoculum tanks will usually be at the most favorable period in 2 to 3 days. Substantial antibiotic activity is obtained in the final fermentor stage in approximately 3 to 5 days. The antibiotic levels range from 50 to 500 mg per liter.

The process of antibiotic production is conveniently followed during fermentation by biological assay of the broth employing a sensitive strain of Staphylococcus aureus or Bacillus subtilis. Standard plate assay technique is employed in which the zone of inhibition surrounding a filter paper disc saturated with the broth is used as a measure of antibiotic potency.

Thin layer chromatography employing silica gel is a useful tool for analyzing the antibiotic produced in fermentation media and the composition of crude and purified materials extracted from the fermentation broths. The thin layer chromatograms, after development with ethyl acetate, are sprayed with 3% vanillin in ethanolic sulfuric acid (98:5:1.5% v/v) followed by heating at 60°–80° C. for a few minutes. The antibiotic is observed initially as a dirty brown spot changing with time to a brilliant purple spot on a white background.

Antibiotic Compound 38,986 may be separated and recovered from fermentation broth by extracting with an organic solvent such as chloroform, ethyl acetate or methyl isobutyl ketone. The major portion of the antibiotic is contained in the mycelium and may be extracted therefrom by slurrying the separated mycelium with a water-soluble solvent such as methanol.

The preferred method of separation and recovery of antibiotic Compound 38,986 is as follows: The whole (unfiltered) fermentation broth is twice extracted with about 1/5 to ½ volume of methyl isobutyl ketone. The solvent extract is concentrated under vacuum to an oily residue which is then slurried with silica gel $PF_{254}$ in heptane and added to a silica gel column (preferably a bed of silicon gel 60 topped with a layer of silica gel $PF_{254}$, both available from E. Merck, Darmstadt, Germany). The silica gel column is successively developed with heptane, benzene, chloroform, chloroform:ethyl acetate (1:1 v/v), ethyl acetate and methanol. The main antibiotic fraction is eluted with chloroform: ethyl acetate (1:1 v/v). The eluate is concentrated under vacuum, taken up in acetone and stirred for about 30–60 minutes with activated charcoal (Darco G 60). The charcoal is removed by filtration, and the solution is concentrated under vacuum to a foam which could not be induced to crystallize.

The antibiotic that is isolated at this stage is a mixture of the free acid and the sodium and potassium salts of Compound 38,986 formed with both sodium and potassium ions occurring in and scavenged from the fermentation broth.

The free acid of Compound 38,986 may be derived from the mixed sodium/potassium salts by adjusting the pH of an aqueous acetone solution of the salts with dilute phosphoric acid. The acetone is then removed in vacuo and the aqueous phase extracted with ethyl acetate. The organic phase after drying over sodium sulfate is evaporated in vacuo to a foam.

The sodium salt of Compound 38,986 may be obtained by adjusting an aqueous acetone solution of the free acid to pH 8.5 with sodium hydroxide. The potassium salt is similarly obtained using potassium hydroxide.

Compound 38,986 and its salts exhibit excellent activity against coccidiosis infections in poultry. When incorporated in the diet of chickens at a level of 50 to 200 ppm, the compounds are effective in controlling single infections of *Kimeria tenella, E. acervulina, E. maxima*, etc. and mixed infections of these organisms.

Because of its end use for the prevention and treatment of coccidiosis in poultry, whole fermentation broth containing Compound 38,986 may be taken to dryness (preferably by spray-drying) and incorporated in poultry feed at the desired antibiotic potency level.

Compound 38,986 and its salts also exhibit excellent activity against actoparasites. For example, the mortality of blowflies which come into contact with a solution of Compound 38,986 in a concentration of 25 ppm is 100%.

Compound 38,986 exhibits inhibitory action against the growth of a number of microorganisms (Table I). The test organism is inoculated in a series of test tubes containing nutrient medium and various concentrations of Compound 38,986 to determine the minimal concentration of the antibiotics in meg/ml which inhibits the growth of the organism over a period of 24 hours.

Table I

| Organism | Compound 38,986 (mixed Na/K salts) | Compound 38,986 (free acid) |
| --- | --- | --- |
| *Trepodern hyodynenterine* | 0.39 | — |
| *Bacteroides fragilis* 78A009 | 6.25 | — |
| *Bacteroides fragilis* 78A014 | 6.25 | — |
| *Bacteroides fragilis* 78A021 | 6.25 | — |
| *Bacteriodes fragilis* 78A024 | 6.25 | — |
| *Staphylococcus aureus* 01A005 | 0.39 | 0.78 |
| 01A052 | 0.39 | 0.39 |
| 01A110 | 0.39 | 0.39 |
| 01A111 | <0.10 | 0.20 |
| 01A087 | <0.10 | 0.78 |
| 01A400 | 0.39 | 0.39 |
| *Streptococcus faccalis* 02A006 | <0.10 | <0.10 |
| *Streptococcus pyogenes* 020203 | <0.10 | <0.10 |
| *Mycobacterium smegratis* 05A001 | 3.12 | 3.12 |
| *Bacillus subtilis* 06A001 | <0.10 | <0.10 |
| *Escherichia coli* 51A229 | >200 | >200 |
| *Pseudomenas aeruginosa* 52A104 | >200 | >200 |
| *Klebsiella pneumoniae* 53A009 | >200 | >200 |
| *Proteus mirabilis* 57C064 | >200 | >200 |
| *Salmonella cholerae-suis* 58B242 | >200 | >200 |
| *Pasteurella multocida* 59A001 | 25 | 25 |
| *Serratia marceseens* 63A017 | >200 | >200 |
| *Enterobacterium acrogenes* 67A040 | >200 | — |
| *Neisseriae sicca* 66C000 | <0.10 | <0.10 |

Efficacy data for compound 38,986 and its salts against coccidiosis infection in chickens are obtained in the following manner. Groups of 3–5 ten day old SPF white leghorn cockerel chicks are fed a mash diet containing Compound 38,986 or one of its salts uniformly dispersed therein. After being on this ration for about 24 hours, each chick is inoculated per os with oocysts of the particular species of Eimeria being tested. Other groups of chicks fed on an antibiotic-free mash diet are similarly infected and serve as infected controls. Non-infected, non-medicated chicks serve as normal controls. The results of treatment are evaluated after 5 days in the case of *E. acervulina* and 6 days for all other Elmeria species.

Table II illustrates the results obtained with the mixed sodium and potassium salts of Compound 38,986.

Table II

| Species infection | Dose (ppm) | Ave. degree of infection* | Ratio* |
|---|---|---|---|
| Eimeria tenella | 200 | 1.30 | 0.37 |
| | 150 | 2.70 | 0.77 |
| | 100 | 1.30 | 0.37 |
| | 75 | 2.70 | 0.77 |
| | 50 | 3.00 | 0.86 |
| Eimeria accryaliae | 200 | 1.00 | 0.50 |
| | 150 | 1.40 | 0.70 |
| | 100 | 2.00 | 1.00 |
| | 75 | 1.20 | 0.60 |
| | 50 | 1.40 | 0.70 |
| Eimeria necatrix | 200 | 0.60 | 0.30 |
| | 350 | 1.80 | 0.90 |
| | 100 | 0.60 | 0.30 |
| | 75 | 1.20 | 0.60 |
| | 50 | 1.40 | 0.70 |
| Eimeria maxima | 200 | 1.60 | 1.00 |
| | 150 | 0.80 | 0.50 |
| | 100 | 0.60 | 0.38 |
| | 75 | 1.20 | 0.75 |
| | 50 | 1.60 | 1.00 |
| Eimeria brunetti | 200 | 0.60 | 0.27 |
| | 150 | 1.00 | 0.45 |
| | 100 | 1.00 | 0.45 |
| | 75 | 0.60 | 0.27 |
| | 50 | 1.40 | 0.64 |
| Mixed Infection (Coccivac D, Sterwine Laboratories, Opelika, Alabama) | 200 | 0.40, 0.0** | 0.20, 0.0 |
| | 150 | 0.80, 0.80 | 0.40, 2.0 |
| | 100 | 0.80, 0.80 | 0.40, 2.0 |
| | 75 | 1.40, 1.20 | 0.70, 3.00 |
| | 50 | 1.40, 0.40 | 0.70, 1.00 |

*The criteria used to measure anticoccidial activity consisted of lesion scores of 0 to 4 for *E. tenella* after J.E. Lynch (A new method for the primary evaluation of anticoccidial activity. Am. J. Vet. Res., 22:324–326, 1961); and 0 to 3 for the other species based on a modification of the scoring system devised by J. Johnson and W. H. Reid (Anticoccidial drugs. Lesion scoring techniques in battery and floor pan experiments in chicks. Exp. Parasit., 28:30–36, 1970). A constant ratio was established by dividing the lesion score of each treated group by the lesion score of the infected control.
**The first number pertains to intestinal lesions and the second number to cecal lesions.

Similar coccidial control may be obtained by incorporating the free acid of Compound 38,986, the sodium salt, or the potassium salt thereof in the poultry diet. An efficient and economical method of treatment comprises the incorporation of dried fermentation medium containing antibiotic Compound 38,986 in the poultry diet at the desired antibiotic potency level.

The insecticidal activity of Compound 58,986 is illustrated by the following tests against a number of insects.

Twenty females of the World Health Organization standard fully-susceptible strain of *Musca domestica*, 2–4 days old, are anaesthetized with carbon dioxide. One microliter of a solution containing Compound 38,986 is applied to the dorsal surface of the thorax. The flies are then maintained in gauze-covered pots at 25° C. and approximately 50% relative humidity for 24 hours with a cotton wool pad moistened with sugar solution and placed on the gauze as food. Twenty flies are treated with solvent only and serve as controls. At the end of this period the mortality is noted and recorded as a percentage after correction for any mortality among the controls.

Five grams of sugar are covered with acetone and treated with 0.5 ml of a solution containing 12.5 to 100 parts per million of Compound 38,986. The acetone is then evaporated off with constant stirring. The sugar bait is then transferred to a plastic pot covered with gauze, and twenty adult female *Lucilia sericata* are introduced. A pad of wet cotton wool provides a free water supply and the insects are maintained for 24 hours and mortalities calculated. The control group comprises twenty flies maintained with untreated sugar.

0.5 ml of Compound 38,986 test solution is pipetted evenly on to Whatman no. 1 filter paper (8 cm. × 6.25 cm.) to give a deposit of 50 to 100 mg/m². When dry, the paper is rolled and slid into a test tube to which is added 1.5 ml of calf serum which is absorbed by the filter paper and serves as food. Fifteen *Lucilia sericata* larvae, approximately 36 hours old, are introduced and the tube closed with a cotton wool plug and stored with the top part only in a strong light to keep the larvae in the lower part of the tube and thus in contact with the filter paper. The insects are maintained for 24 hours, and mortalities calculated. Fifteen larvae confined with untreated filter paper serve as controls.

The test results are tabulated in Table III.

Table III

| Musea domestica (adult) | | Lucilia sericata (adult) | | Lucilia sericata (larvae) | |
|---|---|---|---|---|---|
| Dose (μ)/ferale | % Kill | Dose (ppm) | % Kill | Dose (mg/m²) | % Kill |
| 1 | 100 | 100 | 100 | 100 | 100 |
| 0.5 | 100 | 50 | 100 | 50 | 18 |
| 0.25 | 100 | 25 | 100 | | |
| 0.125 | 40 | 12.5 | 40 | | |

The above test results may be obtained with the sodium salt or the potassium salt of Compound 38,986; a mixture of the free acid, the sodium salt and the potassium salt of Compound 38,986; or dried fermentation medium containing Compound 38,986 or its cationic salts.

EXAMPLE I

A sterile aqueous medium having the following composition was prepared:

| | Grams/liter |
|---|---|
| Glucose | 10.0 |
| Soluble starch | 20.0 |
| Yeast extract | 5.0 |
| Enzymatic digest of casein | 5.0 |
| K₂HPO₄ | 0.4 |
| CaCO₃ | 4.0 |
| pH - 7.0 | |

Cells from a slant of *Streptomyces flaveolus* ATCC 31100 were transferred to a series of 300 ml flasks each containing 50 ml of this sterile medium and shaken on a rotary shaker for 3–4 days at 28°–30° C. Five ml aliquots of this grown inoculum were transferred aseptically to 300 ml flasks containing 100 ml of sterile medium as described above. After shaking for 3–4 days at 28°–30° C., the grown inoculum was transferred to four-liter fermentors containing two liters of the following sterile medium:

| | Grams/liter |
|---|---|
| Glucose | 10.0 |
| Starch | 10.0 |
| Soy flour | 10.0 |
| Grain solubles | 5.0 |
| NaCl | 5.0 |
| CaCO₃ | 1.0 |
| pH - 7.0 | |

The fermentation was conducted for 90–120 hours at 28°–36° C. with stirring at 1700 revolutions per minute and aeration at about one volume of air per volume of broth per minute. Large fermentors containing from 8,000 to 10,000 gallons of medium may be inoculated with about 2% of this growth. The fermentation is conducted until an antibiotic potency of at least 50 mg per liter is obtained (90 to 120 hours).

One hundred liters of whole broth were treated with one-fifth volume of methyl isobutyl ketone and the organic phase separated with the aid of a centrifugal separator. The organic layer derived in this fashion was concentrated in vacuo to an oily residue, 1.5 kilos of which were dispersed on silica gel by its addition in solution in 3 liters of heptane to silica gel $PF_{254}$, 1.5 kilograms, and silica gel 60,250 grams. The resultant slurry was added to a bed of 500 grams of silica gel 60. The silica gel was then washed successively with 2 gallons of heptane, 2 gallons of benzene, 1 gallon of chloroform, 2 gallons of chloroform:ethyl acetate (1:1, v/v), 2 gallons of ethyl acetate and 1 gallon of methanol. The desired antibiotic, Compound 38,986, was found to reside in the chloroform:ethyl acetate (1:1, v/v) wash (93 grams). This was dissolved in 100 ml of heptane and added to a column of silica gel 60 (3 kilos) made up in heptane and the column developed with chloroform containing increasing proportions of ethyl acetate. The appropriate fractions were combined, evaporated in vacuo (19 grams), taken up in acetone, 250 ml, and treated with an equal weight of activated charcoal (Darco G 60) at room temperature for about 60 minutes. Filtration, followed by evaporation in vacuo yielded a foam (18 grams) which could not be persuaded to crystallize. This material was a mixture of the free acid, sodium salt and potassium salt of Compound 38,986.

The physical and chemical data for the material isolated at this stage varies from fermentation to fermentation because of the differing percentages of free acid, sodium salt and potassium salt. The data for two representative samples are shown below:

Sample A is characterized by an average composition by weight of 64.05% carbon and 9.36% hydrogen, an optical rotation of $[\alpha]_D^{25°} = -7.3°$ (c = 1, acetone), and when pelleted in KBr, FIG. 1, exhibiting distinguishable bands in the infrared spectrum over the region 2 to 14 microns at the following wavelengths in microns: 2.98, 3.42, 5.75, 6.12, 6.85, 7.25, 8.65, 9.00, 9.24, 9.40, 9.65, 10.10, 10.40 and 11.17.

Sample B is characterized by an average composition by weight of 66.96% carbon and 9.45% hydrogen, an optical rotation of $[\alpha]_D^{25°} = -2.1°$ (c = 1, acetone), and when pelleted in KBr, FIG. 2, exhibiting distinguishable bands in the infrared spectrum over the region 2 to 14 microns at the following wavelengths in microns: 2.95, 3.40, 5.72, 5.78, 6.35, 6.82, 7.22, 7.57, 7.96, 8.28, 8.65, 8.88, 8.97, 9.22, 9.37, 9.65, 9.82, 10.10, 10.38, 10.82, 11.15, 11.85, 13.37 and 13.72.

Sample A and Sample B are soluble in methanol, ethanol, acetone, chloroform methylene chloride, diethyl ether, ethyl acetate, and methyl isobutyl ketone; partially soluble in heptane; and insoluble in water.

Both samples give the same free acid on treatment with dilute phosphoric acid.

EXAMPLE II

The mixture of the free acid and mixed sodium and potassium salts of Compound 38,986 of Example I was dissolved in aqueous acetone and the pH adjusted to 4.5 with dilute phosphoric acid. The acetone was then removed in vacuo and the aqueous phase extracted with ethyl acetate. The organic phase was then dried over sodium sulfate and evaporated in vacuo to a foam. The free acid could not be induced to crystallize.

The free acid is soluble in methanol, ethanol, acetone, chloroform, methylene chloride, diethyl ether, ethyl acetate and methyl isobutyl ketone. It is partially soluble in heptane and insoluble in water.

The free acid has an optical rotation of $[\alpha]_D^{25°} = 7.5°$ (c = 1, acetone), After drying overnight in vacuo at 70° C. over phosphorus pentoxide, the average composition by weight is 65.11% carbon and 9.54% hydrogen. The free acid of Compound 38,986 possesses no characteristic ultraviolet light absorption pattern.

The infrared spectrum of the free acid of Compound 38,986, FIG. 3, is attached. A KBr pellet shows characteristic absorption in the infrared region at the following wavelengths in microns: 2.98, 3.44, 5.75, 5.78, 6.85, 7.24, 7.98, 8.30, 8.65, 9.00, 9.23, 9.42, 9.67, 9.83, 10.10, 10.38, 10.83, 10.92, 11.18, 11.45, 11.85, 13.40, 13.70 and 14.10.

EXAMPLE III

The sodium salt of Compound 38,986 was obtained from the free acid of Example II by adjusting an aqueous acetone solution of the free acid to pH 8.5 by the addition of 1.0 N NaOH. The acetone was removed in vacuo and the aqueous phase extracted with ethyl acetate to yield a foam which could not be induced to crystallize.

The sodium salt of Compound 38,986 has an optical rotation of $[\alpha]_D^{25°} = -4.9°$ (c = 1, acetone). After drying overnight in vacuo at 70° C. over phosphorus pentoxide, the average composition by weight is 64.15% carbon and 9.44% hydrogen.

The infrared spectrum of the sodium salt of Compound 38,986, FIG. 4, is attached. A KBr pellet shows characteristic absorption in the infrared region at the following wavelengths in microns: 2.95, 3.42, 5.74, 5.78, 6.35, 6.83, 7.23, 7.55, 7.98, 8.27, 8.67, 9.00, 9.25, 9.40, 9.66, 9.84, 10.10, 10.37, 10.80 11.15, 11.45, 11.87, 13.42, 13.70 and 14.05.

EXAMPLE IV

The potassium salt of Compound 38,986 was prepared by the method of Example III employing potassium hydroxide in place of sodium hydroxide. The material was obtained as a foam that could not be induced to crystallize.

The optical rotation is $[\alpha]_D^{25°} = +8.3$ (c = 1, acetone). The average composition by weight of the dried sample is 63.26% carbon and 8.91% hydrogen.

The infrared spectrum of the potassium salt of Compound 38,986, FIG. 5, is attached. A KBr pellet shows characteristic absorption in the infrared region at the following wavelengths in microns: 3.00, 3.45, 5.75, 5.80, 6.40, 6.85, 7.15, 7.27, 7.55, 7.79, 8.00, 8.15, 8.30, 8.74, 9.00, 9.25, 9.67, 9.85, 10.13, 10.42, 10.82, 11.19, 11.40, 11.97, 12.30, 12.90, 13.40 and 14.05.

EXAMPLE V

The method of Example I may be repeated employing clarified fermentation broth in place of whole, unfiltered fermentation broth.

EXAMPLE VI

The mycelium separated from the clarified fermentation broth of Example V may be slurried several times with methanol, the methanol extract concentrated under vacuum and the residue treated by the method of Example I.

EXAMPLE VII

The fermentation process of the method of Example I may be repeated employing a fermentation medium of the following composition:

|  | Grams/liter |
|---|---|
| Glucose | 20.0 |
| Starch | 10.0 |
| Soy flour | 10.0 |
| Grain solubles | 5.0 |
| $Fe_2(SO4)_3$ | 0.2 |
| $MaCl_2$ | 0.2 |
| $CaCO_3$ | 1.0 |
| NaCl | 5.0 |
| Methyl oleate | 2.0 |
| Soybean oil | 2.0 |
| pH - 6.6–6.7 | |

At the end of the fermentation cycle, the whole unfiltered fermentation broth is taken to dryness, preferably by spray-drying.

What is claimed is:

1. The method of controlling coccidiosis in poultry which comprises administering to poultry an effective amount for controlling coccidiosis of antibiotic Compound 38,986, or a pharmaceutically acceptable cationic salt thereof incorporated in the diet of said poultry, said antibiotic compound when in the form as the free acid having an optical rotation of $a_D{}^{25°} = -7.5°$ at a concentration of 1% in acetone; an average composition by weight of 65.11% carbon, 9.54% hydrogen and 25.35% oxygen (by difference); and, when pelleted in KBr, exhibiting characteristic abosrption in the infrared region at the following wavelengths in microns: 2.98, 3.44, 5.75, 5.78, 6.85, 7.24, 7.98, 8.38, 8.65, 9.00, 9.23, 9.42, 9.67, 9.83, 10.10, 10.38, 10.92, 11.18, 11.45, 11.85, 13.40, 13.70, and 14.10.

2. The method of claim 1 wherein said antibiotic compound is the sodium salt of Compound 38,986.

3. The method of claim 1 wherein said antibiotic compound is the potassium salt of Compound 38,986.

4. The method of claim 1 wherein said antibiotic compound is a mixture of the free acid, the sodium salt and the potassium salt of Compound 38,986.

5. The method of claim 1 wherein said antibiotic compound is Compound 38,986.

* * * * *